US00PP26667P2

(12) United States Plant Patent
Smith et al.

(10) Patent No.: US PP26,667 P2
(45) Date of Patent: Apr. 26, 2016

(54) DENDRANTHEMA PLANT NAMED 'ICICLE IGLOO'

(50) Latin Name: *Chrysanthemum×morifolium*
Varietal Denomination: Icicle Igloo

(71) Applicants: Mark A. Smith, Fort Myers, FL (US); Cornelis P. Vandenberg, Fort Myers, FL (US)

(72) Inventors: Mark A. Smith, Fort Myers, FL (US); Cornelis P. Vandenberg, Fort Myers, FL (US)

(73) Assignee: Aris Horticulture, Inc., Barberton, OH (US)

( * ) Notice: Subject to any disclaimer, the term of this patent is extended or adjusted under 35 U.S.C. 154(b) by 140 days.

(21) Appl. No.: 13/998,708

(22) Filed: Nov. 26, 2013

(51) Int. Cl.
*A01H 5/02* (2006.01)

(52) U.S. Cl.
USPC ..... Plt./294

(58) Field of Classification Search
USPC ..... Plt./294, 288
See application file for complete search history.

*Primary Examiner* — Keith Robinson
(74) *Attorney, Agent, or Firm* — C. A. Whealy

(57) ABSTRACT

A new and distinct cultivar of Dendranthema plant named 'Icicle Igloo', characterized by its upright, outwardly spreading and uniformly mounded plant habit; freely branching habit; dense and full plant form; uniform and freely flowering habit; daisy-type inflorescences; white-colored ray florets; and good garden performance and winter hardiness.

1 Drawing Sheet

Botanical designation: *Chrysanthemum×morifolium.*
Cultivar denomination: 'ICICLE IGLOO'.

BACKGROUND OF THE INVENTION

The present invention relates to a new and distinct Dendranthema plant, botanically known as *Chrysanthemum×morifolium*, commercially grown as a perennial garden-type Dendranthema plant, and hereinafter referred to by the cultivar name 'Icicle Igloo'.

The objective of the breeding program is to create new perennial garden-type Dendranthema plants having uniformly mounding plant habit, inflorescences with desirable inflorescence forms, attractive floret colors and good winter hardiness and garden performance.

The new Dendranthema plant originated from an open-pollination in September, 2008 in Bogota, Colombia of a an unnamed proprietary selection of *Chrysanthemum×morifolium*, not patented, as the female, or seed, parent with an unknown selection of *Chrysanthemum×morifolium*, as the male, or pollen, parent. The new Dendranthema plant was discovered and selected by the Inventors as a single flowering plant within the progeny of the stated open-pollination in a controlled greenhouse environment in Smoketown, Pa. on Sep. 28, 2009.

Asexual reproduction of the new Dendranthema plant by vegetative cuttings was first conducted in a controlled greenhouse environment in Smoketown, Pa. since March, 2010 and such asexual propagation has shown that the unique features of this new Dendranthema plant are stable and reproduced true to type in successive generations.

SUMMARY OF THE INVENTION

Plants of the new Dendranthema have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Icicle Igloo'. These characteristics in combination distinguish 'Icicle Igloo' as a new and distinct garden-type Dendranthema plant:

1. Upright, outwardly spreading and uniformly mounded plant habit.
2. Freely branching habit; dense and full plant form.
3. Uniform and freely flowering habit.
4. Daisy-type inflorescences.
5. White-colored ray florets.
6. Natural season flowering occurs about September 20 to 21 in the Northern Hemisphere.
7. Good garden performance and winter hardiness.

Plants of the new Dendranthema differ primarily from plants of the female parent selection in ray floret color as plants of the female parent selection have red-colored ray florets.

Plants of the new Dendranthema can be compared to plants of *Chrysanthemum×morifolium* 'Yovanna', disclosed in U.S. Plant Pat. No. 20,231. In side-by-side comparisons, plants of the new Dendranthema differ from plants of 'Yovanna' in the following characteristics:

1. Plants of the new Dendranthema are larger than plants of 'Yovanna'.
2. Plants of the new Dendranthema are more rounded than and not as upright as plants of 'Yovanna'.

BRIEF DESCRIPTION OF THE PHOTOGRAPHS

The accompanying photographs illustrate the overall appearance of the new Dendranthema showing the colors as true as it is reasonably possible to obtain in colored reproductions of this type. Colors in the photographs may differ slightly from the color values cited in the detailed botanical description which accurately describe the colors of the new Dendranthema plant.

The photograph at the bottom of the sheet comprises a side perspective view of a typical flowering plant of 'Icicle Igloo' grown in a container.

The photograph at the top of the sheet is a close-up view of typical inflorescences of 'Icicle Igloo'.

DETAILED BOTANICAL DESCRIPTION

The aforementioned photographs and following observations and measurements describe plants grown during the early autumn in 25-cm containers in an outdoor nursery in Lancaster, Pa. and under cultural practices typical of commercial garden-type Dendranthema production. During the production of the plants, day temperatures averaged 27.8° C. and night temperatures averaged 15.6° C. Plants were 19 weeks old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Icicle Igloo'.

Parentage:

*Female, or seed, parent.*—Unnamed proprietary selection of *Chrysanthemum×morifolium*, not patented.

*Male, or pollen, parent.*—Unknown selection of *Chrysanthemum×morifolium*, not patented.

Propagation:

*Type.*—Terminal vegetative cuttings.

*Time to initiate roots.*—About four days at temperatures about 21° C.

*Time to produce a rooted young plant.*—About ten to twelve days at temperatures about 21° C.

*Root description.*—Fine, fibrous; typically white in color, actual color of the roots is dependent on substrate composition, water quality, fertilizer type and formulation, substrate temperature and physiological age of roots.

*Rooting habit.*—Freely branching, dense.

Plant description:

*Plant and growth habit.*—Perennial garden-type Dendranthema plant with daisy-type inflorescences; upright, outwardly spreading and uniformly mounding plant habit; strong and vigorous growth habit.

*Branching habit.*—Freely branching habit, about nine primary lateral branches each with multiple secondary and tertiary branches; dense and full plant form; pinching is not required.

*Plant height.*—About 28 cm.

*Plant width.*—About 44 cm.

*Lateral branches.*—Length: About 30 cm. Diameter: About 7 mm. Internode length: About 1.8 cm. Strength: Strong. Texture: Pubescent; longitudinally ridged. Color: Close to 147C.

*Leaves.*—Arrangement: Alternate, simple. Length: About 2.5 cm. Width: About 2.2 cm. Apex: Acute. Base: Attenuate. Margin: Palmately lobed, sinuses between lateral lobes mostly parallel and medium. Texture, upper and lower surfaces: Pubescence; veins prominent on lower surface. Luster, upper and lower surfaces: Matte. Venation pattern: Pinnate. Color: Developing leaves, upper surface: Close to 147A. Developing leaves, lower surface: Close to N138B. Fully expanded leaves, upper surface: Close to 137A; venation, close to 137B. Fully expanded leaves, lower surface: Close to 147B; venation, close to 147C. Leaf petioles: Length: About 9 mm. Diameter: About 2 mm. Aspect: Somewhat upright. Texture, upper and lower surfaces: Pubescent. Color, upper and lower surfaces: Close to 147C.

Inflorescence description:

*Type and arrangement.*—Daisy-type inflorescence form with ligulate-shaped ray florets; disc and ray florets arranged acropetally on a capitulum; inflorescences face mostly upright to outwardly and held above and beyond the foliar plane on strong peduncles.

*Fragrance.*—Faintly fragrant, sour.

*Flowering response.*—Under natural season conditions, plants flower about September 20 to 21 in the Northern Hemisphere.

*Postproduction longevity.*—Inflorescences maintain good color and substance for about six weeks on the plant; inflorescences persistent.

*Quantity of inflorescences.*—Freely flowering habit with about 80 inflorescences developing per lateral branch.

*Inflorescence buds.*—Height: About 1.1 cm. Diameter: About 1 cm. Shape: Oblate, flat-topped. Color: Close to NN155D.

*Inflorescence size.*—Diameter: About 3.7 cm. Depth (height): About 1.6 cm. Disc diameter: About 8 mm. Receptacle diameter: About 1.4 cm. Receptacle height: About 6 mm. Receptacle color: Close to 147B.

*Ray florets.*—Quantity and arrangement: About 84 ray florets develop per inflorescence and arranged in about five whorls. Length: About 1.7 cm; length of fused portion, about 5 mm. Width: About 4 mm. Shape: Ligulate. Apex: Emarginate, minutely tri-dentate. Base: Attenuate. Margin: Entire. Orientation: Initially upright, then about 60° to 70° from vertical; apices angled slightly upright. Texture, upper and lower surfaces: Smooth, glabrous; velvety; longitudinally ribbed. Color: When opening, upper surface: Close to NN155B. When opening, lower surface: Close to NN155C. Fully opened, upper and lower surfaces: Close to NN155D; color does not change with development.

*Disc florets.*—Quantity and arrangement: About 72 fused disc florets develop per inflorescence and massed at the center of the capitulum. Length: About 5 mm. Diameter: Less than 1 mm. Shape: Tubular, elongated. Apex: Five-pointed. Texture, inner and outer surfaces: Smooth, glabrous. Color, immature: Apex: Close to 3C. Mid-section and base: Close to 145D. Color, mature: Apex: Close to 3B. Mid-section and base: Close to 145D.

*Phyllaries.*—Quantity and arrangement: About 20 phyllaries develop per inflorescence and arranged in about 2.5 whorls. Length: About 6 mm. Width: About 2.5 mm. Shape: Elliptical. Apex: Acute. Base: Truncate. Margin: Entire; membraneous. Texture, upper surface: Smooth, glabrous. Texture, lower surface: Pubescent. Color, upper and lower surfaces: Close to 147B.

*Peduncles.*—Length, terminal peduncle: About 5.6 cm. Length, fourth peduncle: About 7.2 cm. Diameter, terminal peduncle: About 1.5 mm. Angle: Mostly upright or curving upright. Strength: Strong. Texture: Pubescent. Color: Close to 147B.

*Reproductive organs.*—Androecium (present on disc florets only): Stamen number: Five per floret. Filament length: About 2 mm. Filament color: Close to 145D. Anther length: About 1.5 mm. Anther shape: Narrowly oblong. Anther color: Close to 14B. Pollen amount: Scarce. Pollen color: Close to 14A. Gynoecium (present on ray and disc florets): Pistil length: About 4 mm. Stigma shape: Bi-parted. Stigma color: Close to 2A. Style length: About 2.5 mm. Style color: Close to 145D. Ovary color: Close to NN155D.

*Seeds and fruits.*—Seed and fruit production has not been observed on plants of the new Dendranthema.

Disease & pest resistance: Resistance to pathogens and pests common to Dendranthema plants has not been observed on plants grown under commercial production conditions.

Garden performance & temperature tolerance: Plants of the new Dendranthema have demonstrated excellent garden performance, are hardy to USDA Zone 5 and tolerate high temperatures of about 37.8° C.

It is claimed:

1. A new and distinct Dendranthema plant named 'Icicle Igloo' as illustrated and described.

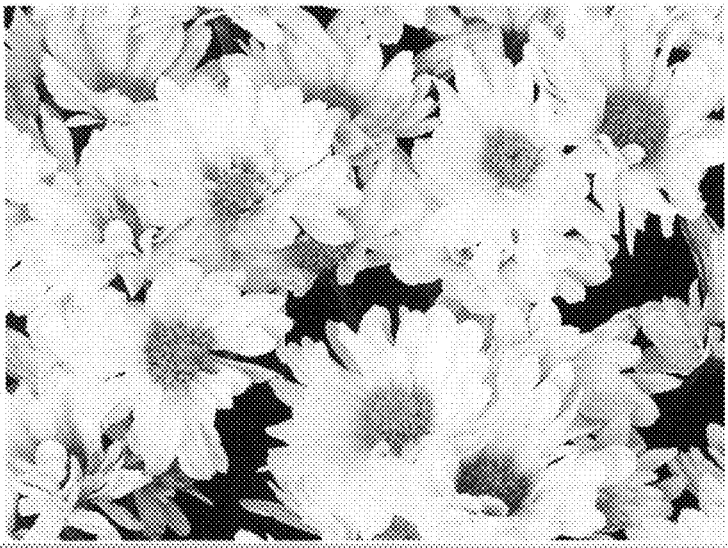
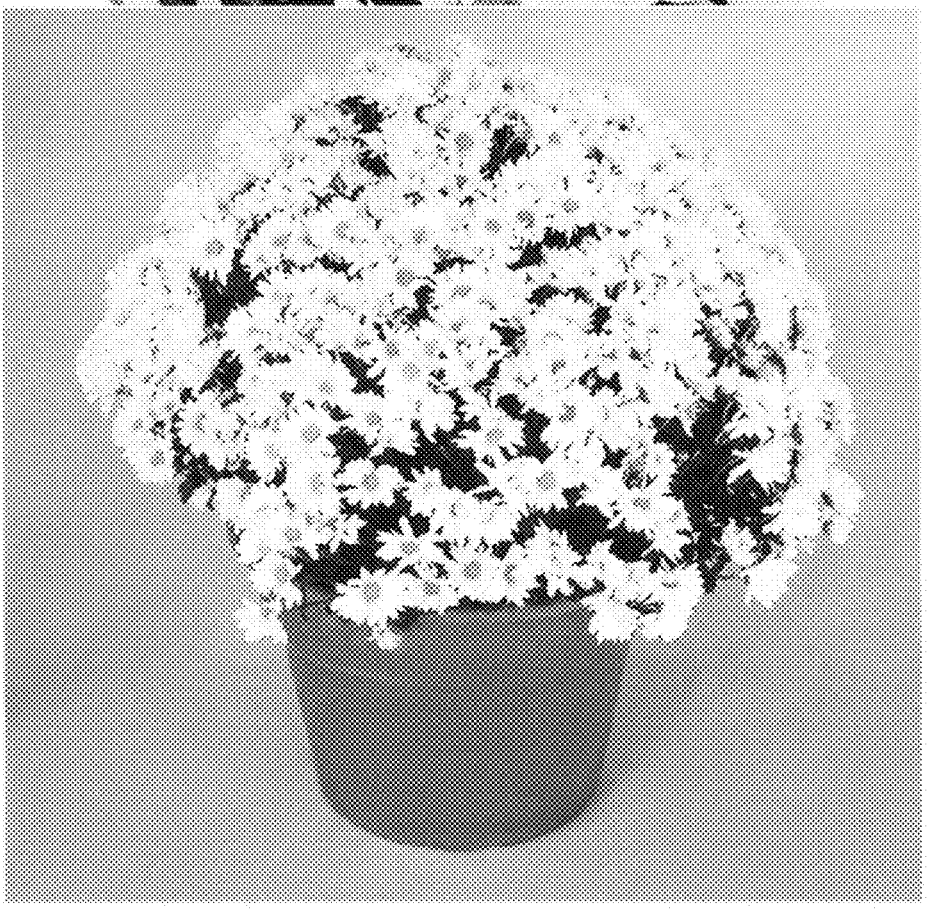

* * * * *